United States Patent [19]

Amir

[11] Patent Number: 5,097,516
[45] Date of Patent: Mar. 17, 1992

[54] TECHNIQUE FOR ILLUMINATING A SURFACE WITH A GRADIENT INTENSITY LINE OF LIGHT TO ACHIEVE ENHANCED TWO-DIMENSIONAL IMAGING

[75] Inventor: Israel Amir, Ewing, N.J.

[73] Assignee: AT&T Bell Laboratories, Murray Hill, N.J.

[21] Appl. No.: 662,583

[22] Filed: Feb. 28, 1991

[51] Int. Cl.⁵ .............................................. G06K 9/00
[52] U.S. Cl. ........................................... 382/1; 382/8; 356/363; 558/101; 558/107
[58] Field of Search .................... 382/1, 8, 30, 34, 48, 382/65, 67; 358/101, 106, 107; 356/376, 383, 357, 358, 363, 370, 371, 372; 250/572, 573, 550, 236

[56] References Cited

U.S. PATENT DOCUMENTS

| | | | |
|---|---|---|---|
| 2,446,628 | 8/1948 | Brown | 356/371 |
| 3,069,654 | 12/1962 | Hough | 340/146.3 |
| 3,692,414 | 9/1972 | Hosterman et al. | 356/371 |
| 3,695,771 | 10/1972 | Bardos | 356/210 |
| 3,794,427 | 2/1974 | Shibata et al. | 356/120 |
| 3,796,500 | 3/1974 | Obser | 356/237 |
| 3,877,814 | 4/1975 | Hess et al. | 356/120 |
| 3,962,681 | 6/1976 | Requa et al. | 340/146.3 H |
| 4,009,965 | 3/1977 | Pryor | 356/363 |
| 4,113,389 | 9/1978 | Kaye | 356/164 |
| 4,131,804 | 12/1978 | Sick et al. | 250/566 |
| 4,139,302 | 2/1979 | Hung et al. | 356/358 |
| 4,240,750 | 12/1980 | Kurtz et al. | 356/394 |
| 4,295,198 | 10/1981 | Copeland | 364/515 |
| 4,319,843 | 3/1982 | Gornall | 356/363 |
| 4,379,308 | 4/1983 | Kosmowski et al. | 358/106 |
| 4,473,842 | 9/1984 | Suzuki et al. | 358/107 |
| 4,545,070 | 10/1985 | Miyagawa et al. | 382/48 |
| 4,569,079 | 2/1986 | Yoshida | 382/1 |
| 4,570,181 | 2/1986 | Yamamura | 358/160 |
| 4,578,810 | 3/1986 | MacFarlane et al. | 382/8 |
| 4,647,208 | 3/1987 | Bieman | 356/375 |
| 4,653,104 | 3/1987 | Tamamura | 382/1 |
| 4,677,473 | 6/1987 | Okamoto et al. | 358/101 |
| 4,696,047 | 9/1987 | Christian et al. | 356/383 |
| 4,731,853 | 3/1988 | Hata et al. | 382/1 |
| 4,731,860 | 3/1988 | Wahl | 382/41 |
| 4,767,212 | 8/1988 | Kitahashi et al. | 358/107 |
| 4,811,410 | 3/1989 | Amir et al. | |
| 4,849,645 | 7/1989 | Mendenko et al. | 250/563 |
| 4,873,651 | 10/1989 | Raviv | 364/513 |
| 4,965,665 | 10/1990 | Amir | 382/8 |

OTHER PUBLICATIONS

B. Carrihill and R. Hummel, Computer Vision, Graphics and Image Processing, 32, 337–358 (1985), "Experiments with the Intensity Ratio Depth Sensor".
W. M. Hastie, Circuits Manufacturing, Feb. 1985, pp. 72–90, "Machine Vision Eyes Loaded Boards".
D. Marro, Research & Development, May, 1985, pp. 114–116, "Does Your PCB Assembly Line Have Eyes?".

Primary Examiner—David K. Moore
Assistant Examiner—Jose L. Couso
Attorney, Agent, or Firm—Robert B. Levy

[57] ABSTRACT

To obtain an enhanced two-dimensional image of a raised, light-reflective reflective feature (12), and its lower height surrounding background such that the contrast between them is enhanced, a line of light having a gradient profile is directed at an acute angle at the feature and its background to illuminate a strip of area thereacross. The reflectance intensity of the illuminated strip will vary in accordance with the height thereof because of the gradient intensity profile of the line of light. When the line of light is spanned across the feature and its background, the resultant image of the feature and its background, captured by spanning a linescan camera (24) thereacross, will exhibit an enhanced contrast between the feature and its background because of the greater height of the feature.

5 Claims, 2 Drawing Sheets

2-D W/GRADIENT-POSITIVE

2-D DIFFUSED LIGHT

TECHNIQUE FOR ILLUMINATING A SURFACE WITH A GRADIENT INTENSITY LINE OF LIGHT TO ACHIEVE ENHANCED TWO-DIMENSIONAL IMAGING

TECHNICAL FIELD

This invention relates to a method and apparatus for achieving an enhanced two-dimensional image of an object such that the object is contrasted from its surrounding background.

BACKGROUND OF THE INVENTION

Machine vision technology is now being employed in many industries for the purpose of rapidly accomplishing inspection of articles with very high accuracy. Within the electronics industry, machine vision systems are currently being employed to inspect populated circuit boards prior to soldering to detect missing and misplaced components as well as to inspect unpopulated boards prior to component placement to detect missing and misplaced solder paste deposits. In U.S. Pat. No. 4,811,410, issued on Mar. 7, 1989, in the names of I. Amir et al. (herein incorporated by reference), there is disclosed a circuit board inspection system comprised of a light source for illuminating a strip of area running across the surface of the board with light of substantially constant intensity. A linescan camera is provided for detecting the intensity of the light reflected from the illuminated strip. The output signal of the camera is processed by a vision system which initially serves to winnow the data so that only the data representing the image of predetermined regions of interest in the strip (where defects are more likely) is retained. The retained data is then processed to detect the presence of defects, if any, in the strip. By simultaneously spanning the circuit board with the light source and the camera, the entire surface of the board can thus be inspected for defects.

While the Amir et al. vision system has proven itself capable of detecting defects such as missing and misplaced components and solder paste deposits, a lack of contrast between the features on the board (i.e., the components and/or solder paste deposits) can adversely affect the accuracy of inspection which is also the case for other conventional inspection systems. Often, the features of interest on the circuit board have a very low contrast with respect to the background and, as a consequence, the intensity of the light reflected from such features is often not appreciably greater than the light reflected from the board itself. Because the contrast between the circuit board and the features of interest is usually not very high, defect detection is difficult.

In an effort to overcome this problem, three-dimensional imaging techniques have been proposed. My co-pending application, Ser. No. 440,948, filed on Nov. 24, 1989, discloses a three-dimensional imaging system, which in a preferred embodiment, comprises a pair of light sources which are separately rendered operative to illuminate a separate one of each first and second spaced-apart strips of area, respectively, on a substrate (e.g., a circuit board) with light. A linescan camera is positioned above the substrate to capture the image of a third strip of area, lying between the first and second strips. When each of the first and second strips is illuminated by a separate one of the first and second lines of light, respectively, the third strip is illuminated with light having a gradient profile. The height of the features (if any) in the third strip can be obtained from the ratio of the sensed reflectance intensities attributed to the first and second light sources, respectively. By separately spanning the substrate with each of the first and second light sources, a three-dimensional image of the entire substrate can be obtained.

While the three-dimensional imaging technique disclosed in my co-pending '948 application advantageously yields information about the height of the features on a circuit board, thereby enabling the presence and position of such features to be more easily established, obtaining a three-dimensional image generally requires additional hardware. Moreover, the three-dimensional imaging systems disclosed in my '948 application may take longer under certain conditions, to produce a three-dimensional image, as compared to the time required for the vision system taught in the '410 system to produce a two-dimensional image.

Thus, there is a need for an improved two-dimensional imaging technique which advantageously enhances the boundary region between an object and its surrounding background to facilitate detection of the presence and position of the object.

SUMMARY OF THE INVENTION

Briefly, in accordance with a preferred embodiment of the invention, a technique is disclosed for obtaining a two-dimensional image of a raised light-reflective topological feature (i.e., a component or a solder deposit) having a greater reflectivity than that of its surrounding, lower height background, to enhance the contrast between the feature and the background. The method is carried out by first illuminating the feature and its surrounding background with a gradient-profile light beam directed thereat at an angle. The intensity of the beam decreases laterally between the beam edges, and therefore the beam is said to have a gradient profile. By illuminating the feature with an angularly-directed gradient-profile beam, the intensity of the light reflected upward by the feature and its surrounding area will be proportional to the height of the feature or surrounding area from which such light is reflected. The image of the feature and its surrounding area illuminated by the gradient-profile beam are captured with an image-acquisition device (e.g., a linescan camera) positioned directly thereabove. The captured image is processed by a vision system which serves to determine the reflectance intensity associated with the feature and its surrounding background. If we assume that the surface reflectance is not much different from the object (otherwise good contrast will be achieved in any event), then the reflectance intensity will be proportional to the height of the feature and surrounding area and a higher reflectance intensity will be associated with the feature than its surrounding background because the feature is presumed to be at a greater height. In this way, the contrast between the feature and its surrounding area is enhanced. Likewise, if the feature is lower, the feature will look duller than its surrounding.

DETAILED DESCRIPTION

Figure 1:
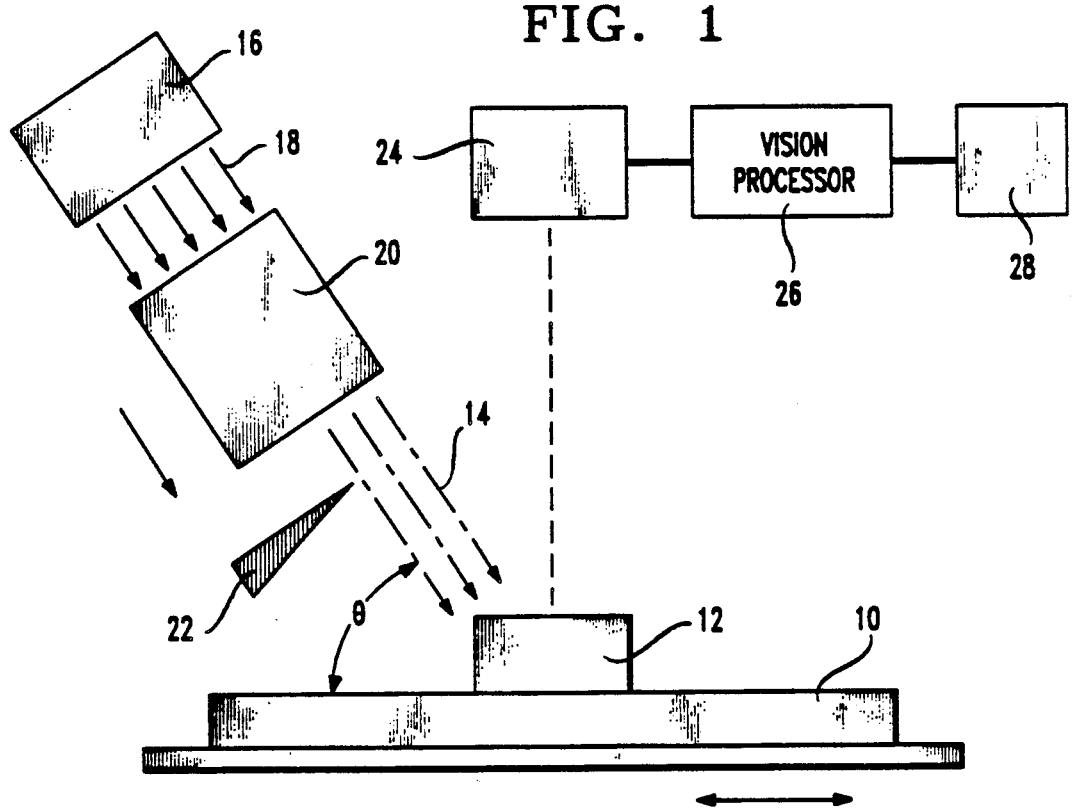
FIG. 1 is a simplified view of a substrate, showing the manner in which the image of a topological feature on the substrate may be may be enhanced by the technique of the present invention.

FIG. 1 is a side view of a substrate 10 (e.g., a circuit board) having at least one raised, light-reflective topological feature 12 on the board surface, such as a solder paste deposit, or an active or passive surface mount component. In the course of fabricating the substrate 10, an inspection is usually carried out to assure that none of the features 12 are missing or mis-positioned. In the event that the feature 12 is a solder paste deposit, it is far less costly to reprint the deposits, should any be found to be missing or misplaced, rather than to wait until after the placement of components on the circuit board. By the same token, it is far less costly to detect missing or misplaced components prior to solder-bonding to the circuit board than afterwards.

Automated inspection of the substrate 10 using a conventional machine vision system, such as the one described in the aforementioned '410 patent, is fraught with the difficulty that the surface of the feature 12 may be diffuse, as is often the case with solder paste deposits and with a large majority of active and passive components. The light reflected vertically upward from feature 12 is often not significantly brighter than that reflected from the surface of the substrate 10 surrounding the feature. The lack of contrast between the feature 12 and the area on the substrate 10 surrounding it makes detection of defects difficult.

Figure 2:
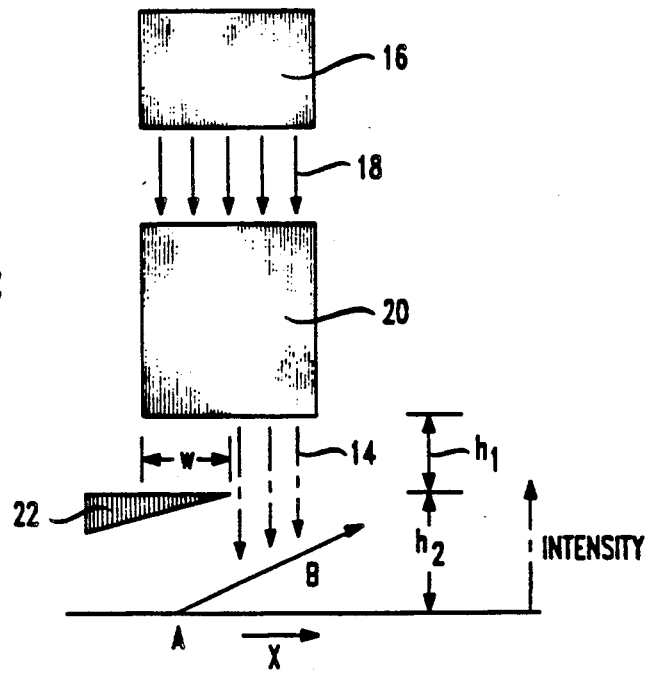
FIG. 2 is a schematic view of a mechanism for generating a gradient profile line of light for enhancing the image in the manner taught in FIG. 1.
Figure 3:
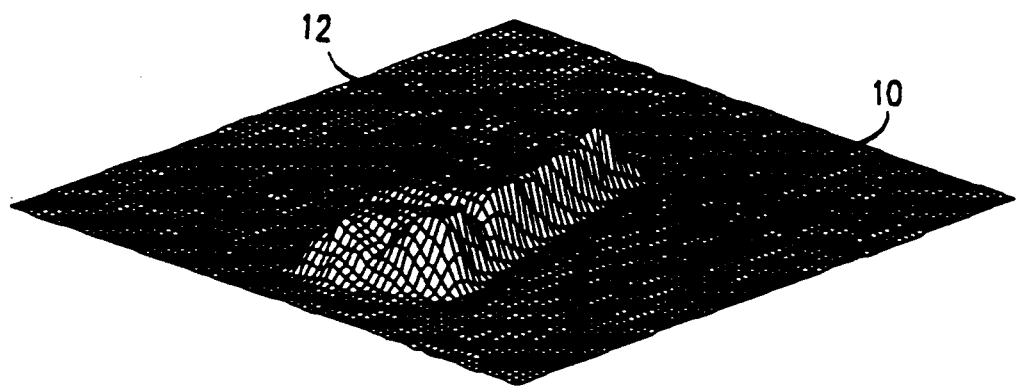
FIG. 3 is a representation of the image of the substrate of FIG. 1 obtained by the enhancement technique of the present invention.

To overcome this difficulty, I have developed a novel technique which advantageously serves to enhance the contrast between the raised, light-reflective topological feature 12 and the substrate 10. Such enhancement may be accomplished, in accordance with my invention, by directing a line of light 14, having a gradient intensity profile, at the feature 12 at an angle $\theta$ relative to the surface of the substrate 10. It is important that the line of light 14, whose longitudinal axis extends into the plane of the drawing, have a gradient profile, that is, an intensity which decreases linearly along the z axis. Referring both to FIGS. 2 and 3, the line of light 14 is generated by a light source 16, typically, a well-controlled mercury or halogen lamp, whose light rays 18 are directed into a circle-to-line converter 20, typically a fiber optic bundle, which transform the rays 18 into the line of light 14 such that the longitudinal axis of the line extends into the plane of the drawing. A generally opaque wedge 22 is placed in front of the circle-to-line converter 22 to partially obstruct the line of line 14 so as to advantageously alter its profile (intensity) so that it is no longer constant but now has a linear gradient.

To understand how the profile of the line of light 14 is altered by the wedge 22, reference should be had to FIG. 2. When placed in front of the circle-to-line converter 20, the wedge 22, which is opaque, partially obstructs the line 14 so that at a point A directly underneath the wedge, no light is received. Conversely, at a point B which lies in the same plane as, but is laterally spaced from, the point A, all of the light from the line of light 14 is received. Within the region between the points A and B, the wedge 22 will obstruct the line of light 14 by creating a shadow in which there is not a sharp transition between light and dark, but rather a more gradual transition. If, in the absence of the wedge 22, the light illuminating the region between A and B would be of uniform intensity (which would be true if the distance between the points A and B is small), then when the wedge is placed in front of the circle-to-line converter 20, the profile of the light illuminating the region between A and B will have a linear gradient.

Assuming that the light striking the region between A and B is uniform in its illumination, the intensity I at any point z in this region will be given by the relationship:

$$I = \frac{I\text{max}}{-A + B} z \tag{1}$$

where Imax is the maximum illumination intensity. Equation (1) can be re-written as:

$$I = \frac{I\text{max}(z - A)}{-A + B} \tag{2}$$

If A is assumed to be zero, and B is defined by the relationship $$B = \frac{w_1 h_2}{h_1} \tag{3}$$

then substituting eq. (3) into eq. (2) yields $$I = \frac{I\text{max } h_1}{h_2 w_1} (z) \tag{4}$$

Thus, the gradient of line of light 14 produced by placing the wedge 22 in front of the circle-to-line converter 20 can be controlled by varying the ratio between $h_1$ to $h_2$. Note that it is possible to place the wedge 22 and the circle-to-line converter 20 as close as possible to the feature 12.

When the gradient-profile line of light 14 is directed at an acute angle at the substrate 10, the intensity I of light reflected vertically upwardly will vary in accordance with the height (z axis position) of the reflecting surface, assuming the reflectivity the substrate is everywhere equal. If the gradient profile of the line of light 14 is assumed to be linear, then the reflectance intensity can be given by the relationship:

$$I(z) = k(ax + b) \tag{5}$$

where a,b and k are constants. The reflecting surface height (Z) varies along the x axis of the substrate 10 because of the presence of the feature 12. Under the conditions depicted in FIG. 1 where the feature 12 is presumed to lie between the coordinates 0 and $x_0$, the reflecting surface height can be given by:

$$Z(x) = u(x) - u(x - x_0) \tag{6}$$

where $$u(x - x_0) = \begin{cases} (1x > 0) \\ (0x \leq x_0) \end{cases}$$

Combining eq. (5) and (6) yields $$I(x) = ka[u(x) - u(x-x_0)] \qquad (7)$$

As may be appreciated from eq. (6), the resultant reflectivity intensity obtained by directing the gradient-profile line of light 14 at the substrate 10 will be greater in the region of the feature 12, owing to its greater height, than in the region surrounding to the feature which is typically of a lower height. The increase in the reflectance intensity attributed to the feature as a consequence of the use of a gradient-profile beam serves to enhance the contrast between the feature and the substrate.

Referring to FIG. 1, in a preferred embodiment, the image of the substrate 10 and the feature 12 is captured with the aid of a linescan camera 24 of a type well known in the art which serves to image a thin strip of area on the substrate running along the y axis parallel to the line of light 14. The output of the camera 24 is coupled to a vision processor 26 identical to the vision processor described in the aforementioned '410 patent. The vision processor 26 serves to process the output signal of the camera 24 to initially winnow the data so that only the image data representative of predetermined regions of interest within the strip imaged by the camera is retained. The retained image data is then processed by the vision processor 26 to determine the intensity of the light reflected from the regions of interest within the strip imaged by the linescan camera 24. A monitor 28 is coupled to the vision processor 24 for displaying reflectance intensity information from the processor. To obtain an image of the entire surface of the substrate 10, it is necessary to span or sweep the substrate with the line of light 14 and the camera 24. Typically, this is accomplished by displacing the substrate 10 along the x-axis with the aid of an x-axis slide 30.

There is a distinct advantage to imaging the substrate with a linescan camera 24 because the linescan camera advantageously serves to capture the image of a thin strip of area running along the y axis. By properly positioning the linescan camera 24, the strip which is imaged thereby can be made to coincide with the strip illuminated by the gradient profile beam of light 14. In this way, the gradient profile of the illumination of the imaged strip will be well defined. In contrast, the use of a two-dimensional array-type camera, in place of the linescan camera 24, would require strongly limiting the allowed gradient (and with it the image enhancement capabilities) in order to avoid camera saturation on one side of the image and a very dull image on the other.

Figure 4:
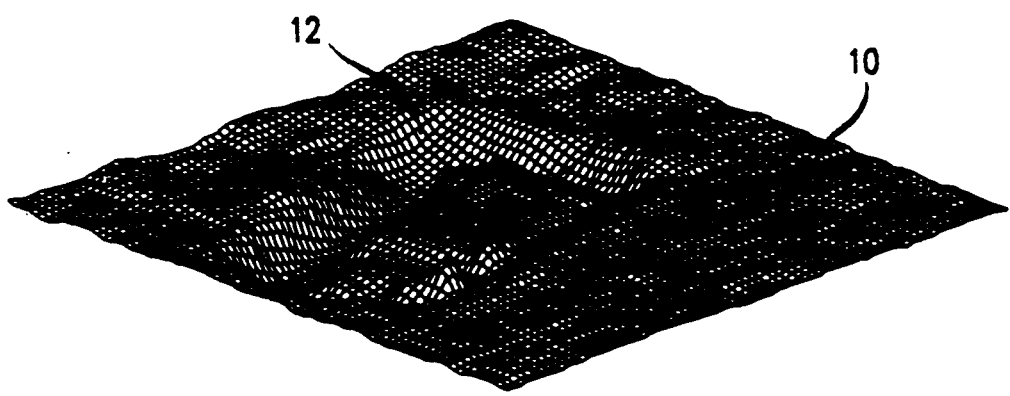
FIG. 4 is a representation of the image of the substrate of FIG. 1 obtained by a conventional two-dimensional imaging system.

FIG. 3 is an image of the substrate 10 and the feature 12 thereon, as captured by the camera 24 and processed by the image processor 24, when the substrate and feature are spanned by the camera and the line of light 14. By contrast, FIG. 4 is an image of the substrate 10 and the feature 12 thereon, as captured by the camera 22 and processed by the image processor 24, when the substrate and feature are spanned by the camera and a line of light having a substantially uniform intensity profile. As compared to FIG. 4, the contrast between the feature 12 and the surrounding area on the substrate 10 surrounding the feature in FIG. 3 is much greater. In fact, as seen in FIG. 4, the contrast between the feature 12 and the area on the substrate 10 surrounding the feature is not very high, making it difficult to distinguish between the feature and the surrounding substrate area.

The foregoing discloses a technique for enhancing the contrast between a light-reflective topological feature and its surrounding background within a captured image by illuminating the feature and its surrounding image with light having a gradient profile.

It is to be understood that the above-described embodiments are merely illustrative of the principles of the invention. Various modifications and changes may be made thereto by those skilled in the art which will embody the principles of the invention and fall within the spirit and scope thereof.

I claim:

1. A method for obtaining a two-dimensional image of a light-reflective topological feature, which is of a different height from a surrounding background, such that the contrast between the feature and its surrounding background is enhanced, comprising the steps of:

generating a line of light, having a gradient intensity profile across its width;

directing the line of light, with its gradient intensity profile, at a light-reflective feature and a surrounding background, which is of a different height, to illuminate a thin strip of area running thereacross such that the intensity of the light striking the feature and its surrounding background varies proportionally with their respective height;

capturing the image of the illuminated strip with a linescan camera;

processing the captured image to detect the intensity of the light reflected therefrom; and spanning the feature and its surrounding background with the line of light and the linescan camera so that a two-dimensional image thereof is obtained so that the contrast between the feature and its surrounding background is enhanced.

2. The method according to claim 1 wherein the line of light is generated by the steps of:

directing a beam of light into a circle-to-line converter to produce a line of light;

placing an opaque object a spaced distance from circle-to-line converter to partially obstruct the line to alter its intensity from being generally uniform to now being gradient in nature.

3. The method according to claim 1 further including the step of adjusting the gradient profile of the line-of-light by varying the ratio of the distance between the opaque object and the circle-to-line- converter to the distance between the wedge and the feature being illuminated.

4. Apparatus for obtaining a two-dimensional image of a light-reflective feature and a surrounding background which is of a different height such that the contrast within the image between the feature and its background is enhanced, comprising:

means for generating a line of light having a gradient intensity profile across its width;

means for directing the line of light with its gradient intensity profile at an acute angle at a feature and a surrounding background, which is of a different height, to illuminate a strip of area thereon such that the intensity of the light reflected from the strip is proportional to its height;

means for capturing the image of the strip illuminated by the line of light;

means for processing the captured image to detect the intensity of the light reflected from the strip illuminated by the line of light; and means for spanning the feature and its surrounding background with the line of light and with the image-capturing means to enable a two-dimensional image of the feature and its surrounding background to be obtained such that the contrast between the feature and its surrounding background is enhanced.

5. The apparatus according to claim 4 wherein the means for directing the line of light comprises:

a light source for producing a light beam;
a circle-to-line converter for converting the light beam into a line of light; and
an opaque wedge placed in front of the circle-to-line converter to partially obstruct the line of light to thereby causing its intensity profile to be gradient in nature.

* * * * *